United States Patent [19]

Okey et al.

[11] Patent Number: 5,731,868

[45] Date of Patent: Mar. 24, 1998

[54] METHOD FOR CHARACTERIZING THE NATURE OF FLUID IN MACHINE FOR WASHING ARTICLES

[75] Inventors: M. Christopher Okey, Minneapolis, Minn.; Margaret M. Ruane, Freeport, Ill.

[73] Assignee: Honeywell Inc., Minneapolis, Minn.

[21] Appl. No.: 795,441

[22] Filed: Feb. 6, 1997

[51] Int. Cl.$^6$ ............................................. G01N 21/00
[52] U.S. Cl. ........................... 356/73; 356/72; 356/442
[58] Field of Search .............................. 356/72, 73, 442, 356/337–343, 246; 250/573–576

[56] References Cited

U.S. PATENT DOCUMENTS

| | | | |
|---|---|---|---|
| 5,291,626 | 3/1994 | Molnar et al. | 356/339 |
| 5,331,177 | 7/1995 | Kubisiak et al. | 250/574 |
| 5,444,531 | 8/1995 | Foreman et al. | 356/341 |
| 5,446,531 | 8/1995 | Boyer et al. | 356/72 |

FOREIGN PATENT DOCUMENTS

6-218183   11/1994   Japan.

*Primary Examiner*—Frank G. Font
*Assistant Examiner*—Amanda Merlino
*Attorney, Agent, or Firm*—William D. Lanyi

[57] ABSTRACT

A method is provided to characterize the nature of a washing fluid by measuring the turbidity and conductivity changes during preselected periods, such as rinse sequences. More specifically, the plateau magnitudes, and variability magnitudes, are measured during each of the rinse sequences of a washing procedure and used as input parameters to a fuzzy logic engine. Calculations are performed in order to characterize the fluid as a function of the input parameters. The characterization of the washing fluid is done in terms of the solubles and suspendeds in the fluid and the cycle state of the fluid. The solubles represent chemical elements in solution within the washing fluid and the suspendeds are particulate matters suspended in the fluid. The cycle state represents the aggregation of the solubles and suspendeds in the fluid.

20 Claims, 10 Drawing Sheets

METHOD FOR CHARACTERIZING THE NATURE OF FLUID IN MACHINE FOR WASHING ARTICLES

BACKGROUND OF THE INVENTION

1. Field of the Invention

The present invention is generally related to a system for characterizing the nature of fluid in a machine for washing articles and, more particularly, to a wash process sensor that is able to measure both turbidity and conductivity and then calculate one or more characteristics of the wash water for the purpose of allowing a controller of the machine for washing articles to more efficiently determine the appropriate number, order and type of sequences of a wash cycle that will most efficiently and effectively cleanse the articles.

2. Description of the Prior Art

Various machines for washing articles, including dishwashers and clothes washers, have been improved by the use of various devices that are able to measure certain parameters regarding the fluid used to wash the articles. The measurements of turbidity and conductivity are well known to those skilled in the art. In addition, it is well known to use fuzzy logic for the purpose of calculating parameters regarding the operation of an appliance.

U.S. Pat. No. 5,291,626, which issued to Molnar et al on Mar. 8, 1994, describes a machine for cleansing articles. The machine, which can be a dishwasher, incorporates a device for measuring the turbidity of a partially transparent liquid. The device includes a sensor for detecting scattered electroradiation and a sensor for detecting transmitted electromagnetic radiation.

U.S. Pat. No. 5,446,531, which issued to Boyer et al on Aug. 29, 1995, discloses a sensor platform, or wash process sensor, for use in machines for washing articles. A plurality of fluid condition sensors are combined together to provide a sensor cluster that senses turbidity, temperature, conductivity and the movement of a ferromagnetic object. The plurality of sensors are attached to a substrate and encapsulated, by an overmolding process, with a light transmissive and fluid impermeable material. The sensor cluster can be disposed at numerous different locations within a body of fluid and does not require a conduit to direct the fluid to a particular location proximate the sensor. In a preferred embodiment of the sensor platform, a circuit is provided which monitors the signal strength of first and second light sensitive components to determine turbidity and, in addition, those signal strengths are also used to advantageously determine the most efficient magnitude of current necessary to drive a lights source, such as a light emitting diode. By controlling the current to a light emitting diode as a function of the strength of light signal received by first and second light sensitive components, the turbidity sensor can be operated at a more efficient and effective level.

U.S. Pat. No. 5,444,531, which issued to Foreman et al on Aug. 22, 1995, discloses a device similar in structure and operation to the device described above in conjunction with U.S. Pat. No. 5,446,531. The Foreman et al patent focuses specifically on the current control regarding the light emitting diode.

U.S. Pat. No. 5,331,177, which issued to Kubisiak et al on Jul. 19, 1995, discloses a turbidity sensor with analog-to-digital conversion capability. The turbidity sensor is provided with a light source and a plurality of light sensitive components which are disposed proximate a conduit to measure the light intensity directly across the conduit from the light source and at an angle therefrom. The conduit is provided with a plurality of protrusions extending radially inward from the walls of the conduit to discourage the passage of air bubbles through the light beam of the sensor. The direct light beam and scattered light are compared to form a relationship that is indicative of the turbidity of the liquid passing through the conduit. The rate of change of turbidity is provided as a monitored variable.

The United States patents cited above are hereby expressly incorporated for reference in this description.

In clothes washing machines, the liquid used to clean the clothes becomes soiled as the cleansing operation proceeds. It would be significantly beneficial if a method could be provided to characterize the nature of the soil in the liquid so that a controller of the machine for washing articles could maximize the efficiency and effectiveness of the selection of cycle elements, or sequences, such as washing, rinsing and spinning, as well as the actions and operations that make up sequences.

SUMMARY OF THE INVENTION

The present invention uses measurements relating to the turbidity and conductivity of a wash fluid in order to calculate certain characteristics of the fluid. A preferred embodiment of the method of the present invention comprises the steps of measuring a first parameter relating to a turbidity of the fluid and measuring a second parameter relating to the conductivity of the fluid. The preferred embodiment of the present invention further comprises the steps of calculating a first characteristic of the fluid as a function of both the first and second parameters and then calculating a second characteristic of the fluid as a function of both of the first and second parameters, and then calculating a third characteristic of the fluid as a function of both the first and second parameters. After the first, second, and third characteristics are calculated, the method of the present invention further comprises the step of providing an output signal which is representative of the first, second, and third characteristics. The output signal is then transmitted to a controller of a machine for washing articles.

The first parameter that is measured by the method of the present invention comprises a first magnitude representative of a plateau value of turbidity during a first preselected time period and a second magnitude representative of a variability value of turbidity during a second preselected time period. The second parameter comprises a third magnitude representative of a plateau value of conductivity during a third preselected time period and a fourth magnitude representative of variability value of conductivity during a fourth preselected time period.

The first characteristic can be representative of the magnitude of particulates suspended in the fluid. The second characteristic can be representative of the magnitude of elements in solution within the fluid. The third characteristic can be representative of the cycle state which is the overall magnitude of foreign matter in the fluid. Fuzzy logic techniques can be used to calculate the first, second and third characteristics, but this is not a requirement in all embodiments of the present invention.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Throughout the Description of the Preferred Embodiment, like components will be identified by like reference numerals.

Figure 1:
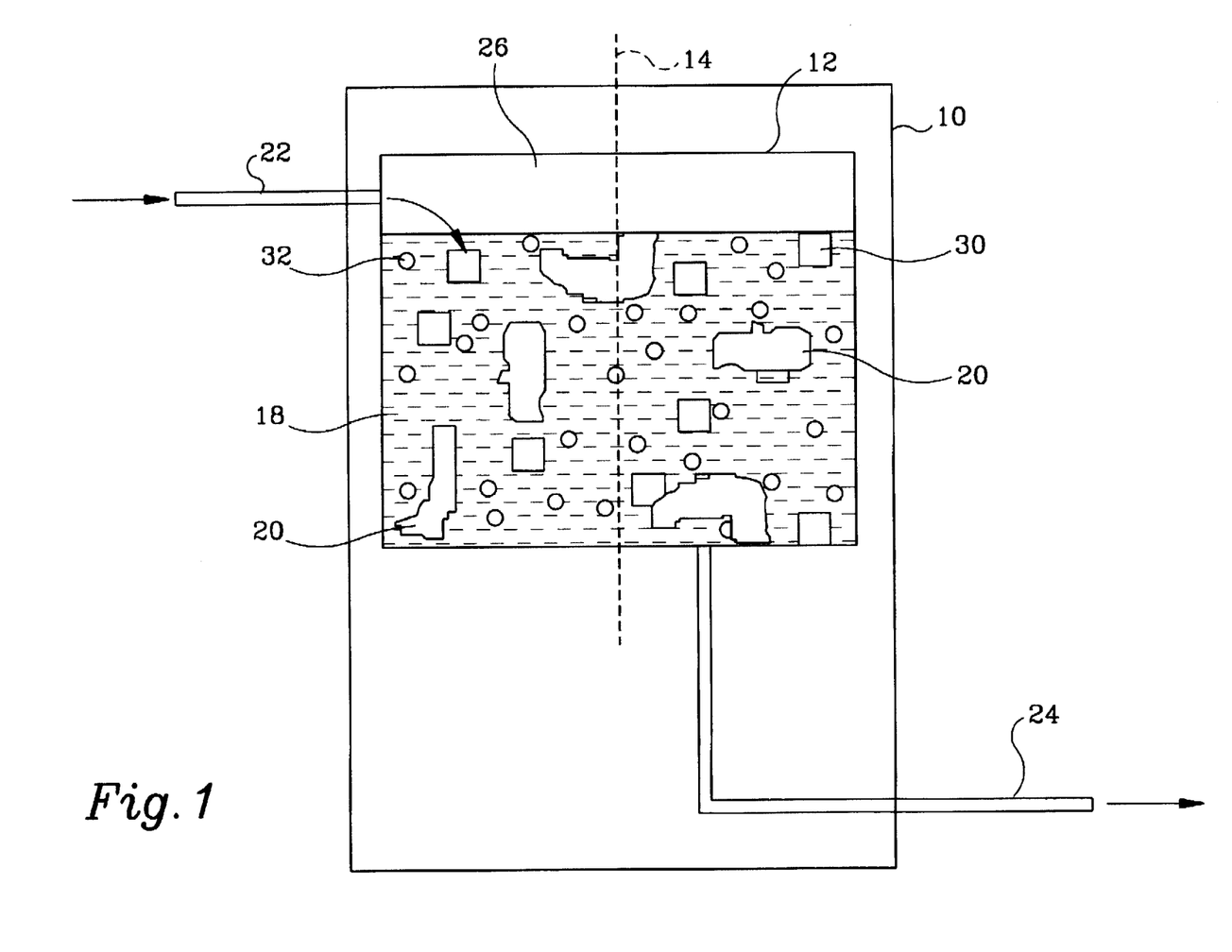
FIG. 1 is a schematic representation of a washing machine.

FIG. 1 is a highly schematic representation of a clothes washer 10. Within the structure of the clothes washer 10, a tub 12 is mounted for rotation about a central axis 14.

Although the tub 12 is illustrated in FIG. 1 as being rotatable about a vertical axis 14, it should be understood that alternative embodiments of the present invention could be applied to machines for washing articles in which the axis of rotation 14 is horizontal. In addition, it should be understood that alternative embodiments of the present invention could be applied to machines for washing articles in which there is no axis of rotation, but a quantity of fluid is transported about the articles by some method. Within the tub, a quantity of fluid 18, such as water, can be used to cleanse articles 20.

The method of the present invention utilizes a wash process sensor, such as that described in U.S. Pat. Nos. 5,444,531 and 5,446,531. A wash process sensor of the type described in these cited United States patents can be disposed within the volume of water 18 or within a conduit connected in fluid communication with the volume of water 18. An inlet conduit 22 and an outlet conduit 24 are provided for filling and draining the tub 12.

In FIG. 1, the tub is shown as being partially filled with water 18 and with an ullage 26 above the water level. The wash process sensor, described above in reference to the cited patents, is able to measure both turbidity and conductivity of the fluid. The wash process sensor can provide a beam of radiation, such as light, which is directed into a detection zone. Light sensitive components can be used to measure the transmitted light and the reflected light from the light source. A magnitude representing the turbidity of the fluid can be determined by dividing the magnitude of scattered light by the magnitude of transmitted light. Alternative methods are also known to those skilled in the art. For example, in certain applications, only scattered light is required to determine a variable that is representative of the turbidity of the fluid. In the following description of the present invention, it will be assumed that a value of turbidity is determined by measuring both scattered and transmitted light from a light source and then dividing the scattered light magnitude by the transmitted light magnitude.

In a preferred embodiment of the present invention, the parameter relating to the turbidity of the fluid actually consists of two values. The first value is a first magnitude which is representative of the value of turbidity settled to during a first preselected time period. This value is referred to herein as turbidity plateau. The first parameter, relating to turbidity, also comprises a second magnitude which is representative of a variability of turbidity during a second time period. In a preferred embodiment of the present invention, the first and second time periods are coincident. The second parameter, which relates to conductivity, also comprises two values. One is a third magnitude which is representative of the value of conductivity settled to during a third preselected time period. This value is referred to herein as conductivity plateau. The other is a fourth magnitude representative of a variability of conductivity during a fourth time period. The third and fourth time periods, in a preferred embodiment of the present invention, are coincident. Furthermore, in a preferred embodiment of the present invention, the first, second, third and fourth time periods are coincident and equal to a rinse sequence.

Using the magnitudes of the plateau of turbidity, the variability of turbidity, the plateau of conductivity, and the variability of conductivity, the present invention calculates three characteristics of the fluid 18 as a function of these turbidity and conductivity parameters. One characteristic relates to the amount of particulates that are suspended in the fluid 18. The second characteristic relates to the chemicals or elements in solution within the fluid 18. The third characteristic relates to the aggregation of suspendeds and solubles in the fluid 18. The first characteristic relating to the particulates in suspension is referred to herein as the magnitude of suspendeds. The second characteristic relating to the magnitude of elements in solution is referred to herein as the magnitude of solubles. In FIG. 1, reference numeral 30 is used to identify the suspendeds and reference numeral 32 is used to identify the solubles. The third characteristic relating to the overall quantity of foreign matter is referred to herein as cycle state.

It should be understood that the wash water used to cleanse articles in a clothes washer can become contaminated in various ways. Depending on the type and amount of soil in the clothes prior to the washing procedure, the wash process may cause the water to contain a greater number of suspendeds, but with very few solubles. On the other hand, the type and amount of soil in the clothes may cause the water to contain a greater number of solubles, but with very few suspendeds. The type and amount of detergent and other materials used for the washing process can have the same effect. The type and amount of detergent and other materials used for the washing process in combination with the soil can have the same effect. The type and amount of the articles themselves can have the same effect. The construction of an efficient clothes washing cycle is dependent on knowledge of the amounts of suspendeds and solubles in the wash water or the articles. The present invention estimates the amounts of suspended and solubles and cycle state found in the wash water.

It should be understood that the suspendeds and solubles can exist both in the wash water 18 and in the articles 20 being washed. In the washing process, the suspendeds and solubles can result from the soil in the articles alone, from the detergent and other materials used for the washing process alone, from both the soil and the detergent in combination, or from the articles themselves. The present invention estimates the amounts of suspendeds and solubles in the fluid 18, and estimates the cycle state in order to provide information to a controller which allows the controller to optimize the selection of sequences of the washing process. For example, in constructing a cycle, the controller can select from wash, rinse and spin sequence for the purpose of removing suspendeds and solubles from the washing load. For example, in addition, the controller can select specific actions for a specific sequence, such as water level, time, or spin speed, for the purpose of removing suspendeds and solubles from the washing load.

Various parameters relating to turbidity and conductivity can be used to describe the conditions of the wash process fluid 18. Particles in suspension, or suspendeds 30, are primarily turbid, but may have some conductive properties. The converse is true for the solubles 32. Solubles are primarily conductive, but may have some properties that are turbid. The cycle state as an aggregation of suspendeds and solubles must take this relationship into account. Because of these characteristics of the solubles and suspendeds, the present invention uses fuzzy logic procedures in its most preferred embodiment.

A typical washing process or wash cycle utilized by a machine for washing articles is divided into washing, rinsing and possibly spinning sequences. The washing sequences typically take place at the start of the cycle and use water, detergent, mechanical action, and possibly heat to release the soil or foreign material from the articles 20. The rinsing sequences typically take place later in the washing cycle and use water, mechanical action, and possibly heat to remove soil and detergent or foreign material from the articles 20. The spinning sequences, if appropriate, typically take place in between and at the end of rinsing sequences, and extract the wash process water from the articles 20. The method of the present invention allows a controller to optimize the sequences of the cycle.

Figure 2:
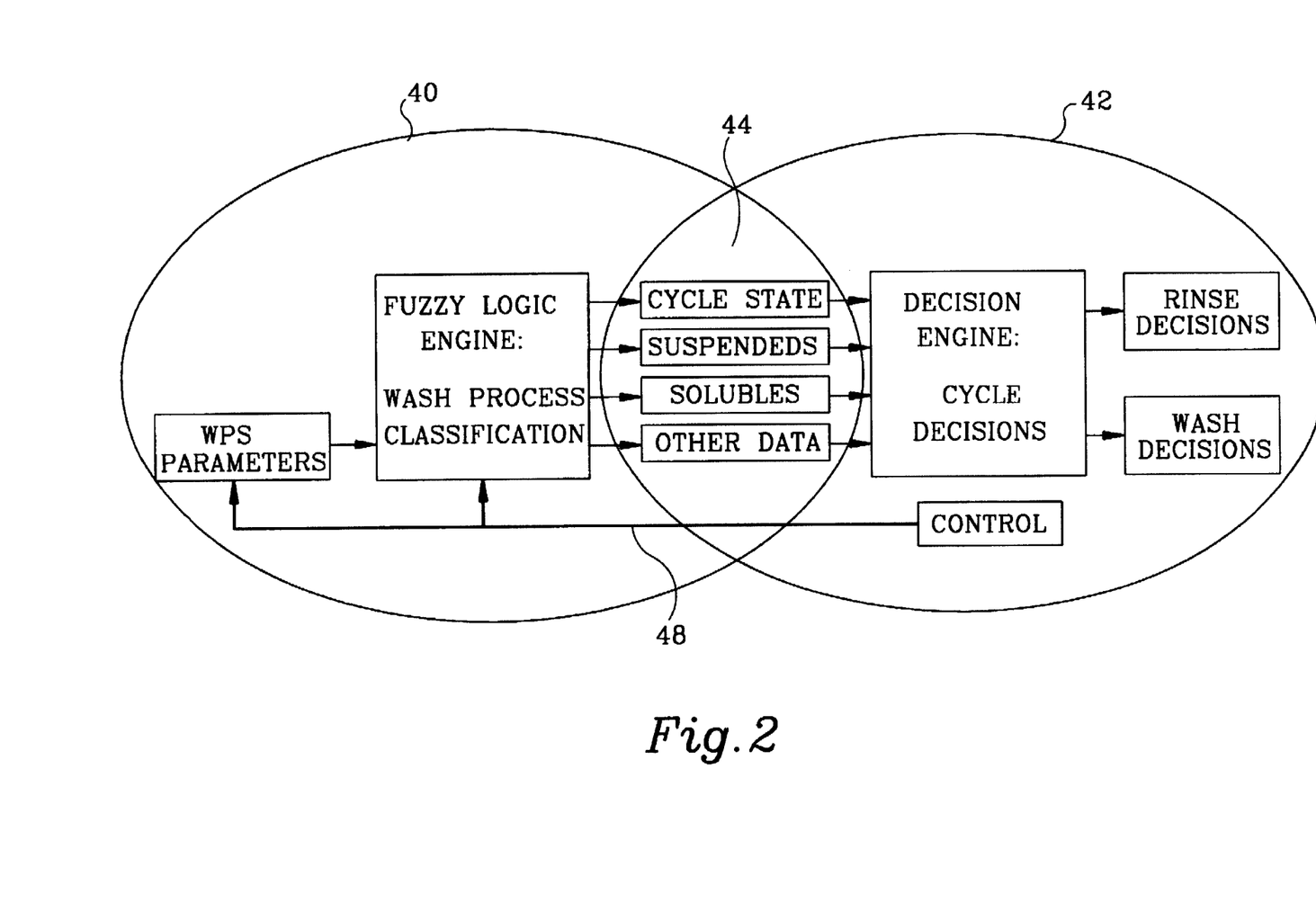
FIG. 2 illustrates the relationship between a wash process sensor and a control system for a washing machine.

It should be understood that the present invention relates to the method by which the nature of the fluid 18 is characterized. It does not, in itself, actually control the washing, rinsing and spinning sequences of the machine. That type of cycle control is typically performed by the controller of the washing machine. The present invention is a method by which the controller can be provided with appropriate information to allow it to optimize performance of the washing machine. FIG. 2 illustrates this relationship.

The venn diagram in FIG. 2 shows the relationship between the operation of the wash process sensor, calculation of the WPS parameters, and the calculation of the fluid characterizations (i.e. suspendeds, solubles, and cycle state) identified by set 40 and the elements of the appliance controller identified by set 42. As illustrated in the venn diagram of FIG. 2, the two sets share several elements. Namely, the fluid characterizations cycle state, suspendeds, and solubles, as well as other data which are illustrated in the subset portion identified by reference numeral 44. Fluid characterizations are the result of the wash process classification fuzzy logic engine, which has as inputs the wash process sensor parameters, which has as inputs the wash process sensor signals. Other data are signals from any step in this process. In addition, it should be noted that the appliance controller also provides control signals, represented by reference numeral 48, which cause the wash process sensor system to respond by taking signals, or causes the calculation of new parameters, or causes the calculation of new characterizations. As illustrated in FIG. 2, the wash process sensor system set 40 and the appliance controller set 42 work together in order to appropriately control the order and the actions of the sequences of the washing machine. However, it should be clearly understood that the present invention describes wash process sensor system portion of the illustration set 40. It relates most directly to the measurement of several signals, calculation of several parameters, and the calculation of several characterizations as a function of those parameters.

Figure 3:
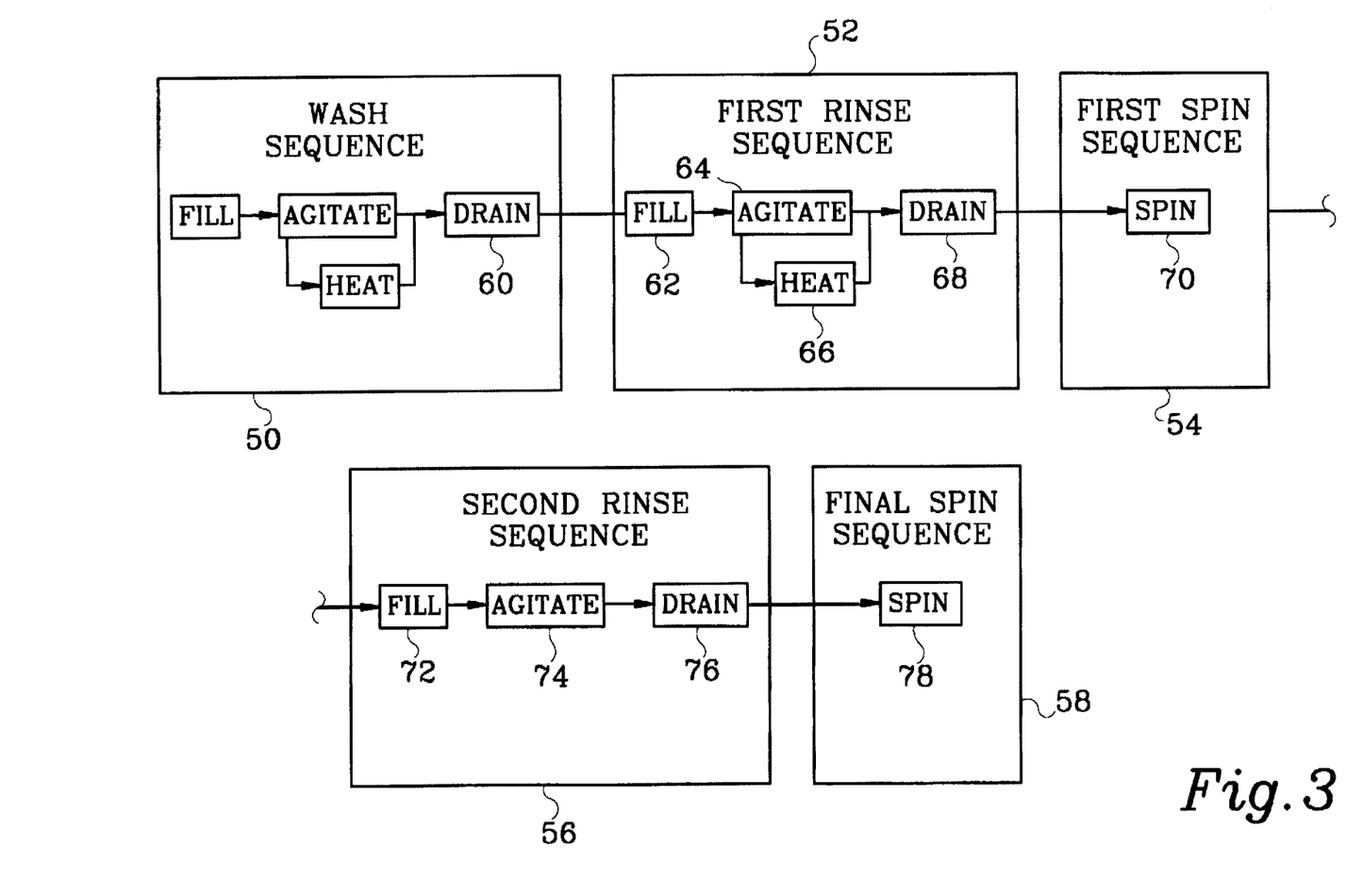
FIG. 3 shows the breakdown of an example wash cycle into its sequences, and the sequences into their actions.

FIG. 3 is a flow chart of an example wash cycle. The chronology identified in FIG. 3 will be used throughout the following description of the present invention. The number, order, and type of sequences that make up a wash cycle varies from manufacturer to manufacturer. This example wash cycle contains one wash sequence 50, two rinse sequences, 52 and 56, and two spin sequences, 54 and 58. Sequences in a wash cycle are composed of actions. The number, order, and type of actions that make up a sequence varies from manufacturer to manufacturer. The wash sequence 50, in this example, is composed of a fill action, an agitate action, a heat action, and a drain action 60. The first rinse sequence 52, in this example, is composed of a fill action 62, an agitate action 64, a heat action 66, and a drain action 68. The first spin sequence 54 is composed of a spin action 70. The second rinse sequence 56, in this example, is composed of a fill action 72, an agitate action 74, and a drain action 76. The final spin sequence 58 is composed of a spin action 78.

Actions in a sequence are composed of operations. The number, order, and type of operations that make up an action varies from manufacturer to manufacturer. The fill action, in the wash and rinse sequences, is the operation of opening and then closing an inlet valve so that a desired amount of water enters the tub. The agitate action, in the wash and rinse sequences, is the operation of rotating the tub about its axis in a specific manner to impart mechanical action to the wash articles in the tub. The heat action, in the wash and rinse sequences, is the operation of turning on and turning off a heating element to add thermal energy to the water and washing articles contained in the tub. This results in an increase in temperature of the wash water and the wash articles. The heat action and agitate action, in this example, are coincident. The drain action, in the wash and rinse sequences, is the operation of turning on and turning off a drain pump to remove a desired amount of water from the tub. The spin action, in the spin sequence, is the operation of rotating the tub about its axis at a desired speed to use centrifugal force to extract the wash water from the articles in the tub.

The present invention processes wash process sensor information accumulated during agitate actions, and at a specified point in time classifies the wash process water. The appliance manufacturer uses this classification in deciding how to construct an effective and efficient wash cycle. The appliance manufacturer constructs a wash cycle by choosing the number, order, and type of sequences, the number, order, and type of actions in each sequence, and the number, order, and type of operations for each action.

Figure 4:
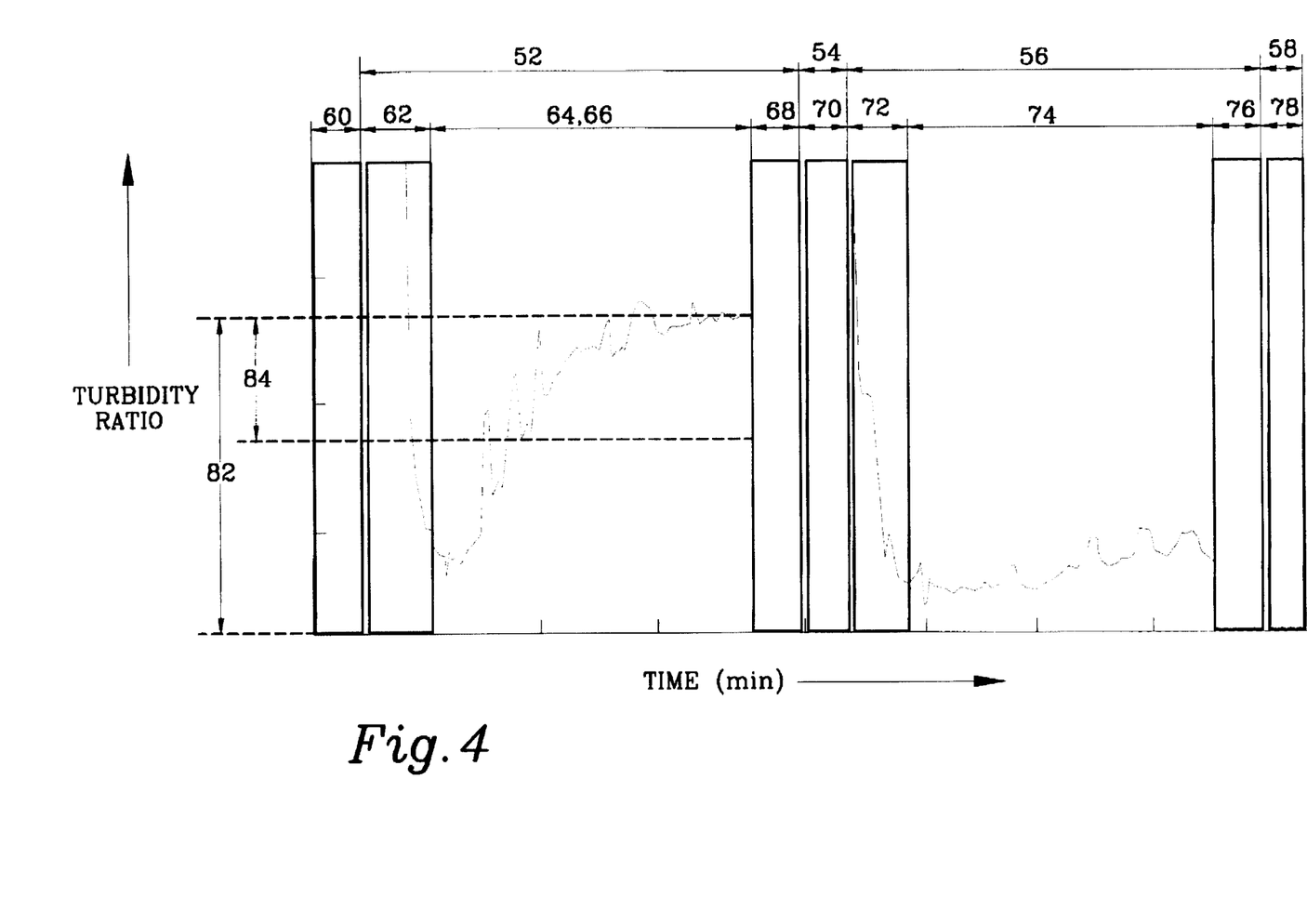
FIG. 4 shows the turbidity measurement for wash fluids during a washing procedure as a function of time.

FIG. 4 represents the turbidity ratio of the fluid 18 in the tub 12 during the time period from the start of the drain action 60 of the wash sequence 50 to the spin action 78 of the final spin sequence 58. The turbidity ratio can be determined by dividing the amount of scattered light by the amount of transmitted light from the wash process sensor, as described above, or by any appropriate and reasonable method known to those skilled in the art. As can be seen in FIG. 4, the turbidity ratio measurement 80 is most prominent during the agitate actions, 64 and 74, of the cycle. During the fill actions, 62 and 72, of the cycle, the turbidity ratio measurement 80 approaches from its maximum value and by the end of the action stabilizes at a true turbidity ratio value. This is caused by the mechanics of the washing machine of this example. The wash process sensor is located such that at the start of the fill action, 62 and 72, it is exposed to air, and in the course of a fill action, 62 and 72, becomes emersed in the wash process water. During the spin actions, 70 and 78, and drain actions, 60, 68 and 76, the turbidity ratio measurement 80 is zero because sensor values are not taken during these actions.

In a preferred embodiment of the present invention, the wash process sensor measures a first parameter that relates to the turbidity.

It can be seen in FIG. 4 that the turbidity ratio, as represented by line 80, levels off at the end of the agitate actions, 64 and 74. The first parameter is comprised of a first magnitude that is representative of this plateau value of turbidity ratio.

In FIG. 4, this turbidity ratio plateau for the first rinse sequence 52 might be represented by the dimension 82. The turbidity ratio plateau value 82 is determined at the end of a first preselected time period which, in this example, is the time period of the first rinse sequence agitate action 64. This time period can be divided into equally spaced time intervals. During each time interval, a turbidity ratio minimum value is detected and stored. At the end of the time period, the stored turbidity ratio minimum values are filtered. The filtering technique can include the taking of the four most recent turbidity ratio minimum values that have been saved, removing the smallest turbidity ratio minimum value, and taking the average of the three remaining turbidity ratio minimum values.

It can be seen in FIG. 4 that the turbidity ratio, as represented by line 80, is jagged during the agitate actions, 64 and 74. These rapid localized variations in turbidity ratio are caused by several factors. First the physical structure of the washing machine can have certain effects on the turbidity ratio being sensed by a wash process sensor. The wash process sensor may be shaped to cause certain streams of fluid to move through the sensing zone while others are diverted. In addition, changes in the agitation motion can effect the turbidity ratio measurements by either increasing the speed of fluid moving through the sensing zone or slowing it. Regardless of the specific causes, rapid localized changes in turbidity ratio as indicated by the jaggedness of the line 80 can be detected. The first parameter is comprised of a second magnitude that is representative of this variability value of turbidity ratio.

In FIG. 4, this turbidity ratio variability for the first rinse sequence 52 might be represented by the dimension 84. The turbidity ratio variability value 84 is determined at the end of a first preselected time period which, in this example is the time period of the first rinse sequence agitate action 64. This time period can be divided into equally spaced time intervals. During each time interval, a minimum turbidity ratio value and a maximum turbidity ratio value are detected. At the end of each time interval, the difference between the maximum value and the minimum value is calculated and stored. At the end of the time period, the stored turbidity ratio difference values are filtered. The filtering technique can include the taking of the four largest turbidity ratio difference values that have been saved, removing the largest turbidity ratio difference value, and taking the average of the three remaining turbidity ratio difference values.

Figure 5:
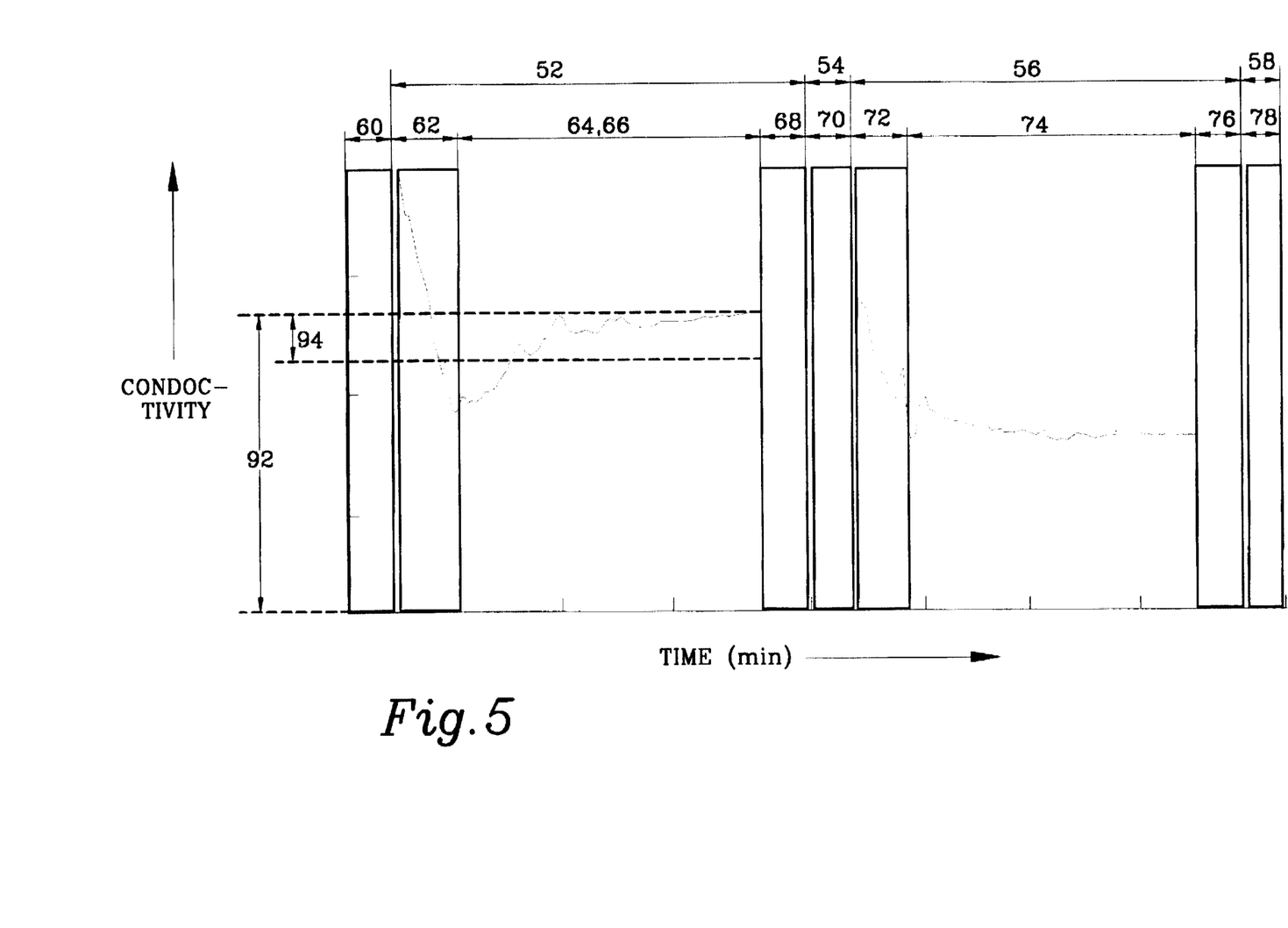
FIG. 5 shows the conductivity measurements of wash fluids as a function of time.

FIG. 5 represents the conductivity of the fluid 18 in the tub 12 during the time period from the start of the drain action 60, of the wash sequence 50 to the spin action 78 of the final spin sequence 58. As can be seen in FIG. 5, the conductivity measurement 90 is most prominent during the agitate actions, 64 and 74, of the cycle. During the fill actions, 62 and 72, of the cycle, the conductivity measurement 90 approaches from a high value and by the end of the action stabilizes at a true conductivity value. This is caused by the mechanics of the washing machine of this example. The wash process sensor is located such that at the start of the fill action, 62 and 72, it is exposed to air, and in the course of a fill action, 62 and 72, becomes emersed in the wash process water. During the spin actions, 70 and 78, and drain actions, 60, 68 and 76, the conductivity measurement 90 is zero because sensor values are not taken during these actions.

In a preferred embodiment of the present invention, the wash process sensor measures a second parameter that relates to the conductivity.

With reference to FIG. 5, the conductivity measurements are taken in a similar manner to those described above in conjunction with FIG. 4. The second parameter comprises a third magnitude that is representative of a plateau value of conductivity. For example, the conductivity plateau for the first rinse sequence 52, might be represented by the dimension 92. The second parameter comprises a fourth magnitude that is representative of a variability value of conductivity. For example, the conductivity variability for the first rinse sequence 52 might be represented by the dimension 94. The first and second parameters are also measured for the second rinse sequence.

It should be understood that many other specific techniques can be employed to measure the four magnitudes that comprise the first parameter relating to turbidity and the second parameter relating to conductivity. The wash process sensor, as described in detail in U.S. Pat. Nos. 5,444,531 and 5,446,531, is used to provide certain basic sensor signals relating to turbidity and conductivity. Typically, the turbidity signal is determined by dividing a scattered light intensity by a transmitted light intensity. The turbidity and conductivity signals, as described above in conjunction with FIGS. 4 and 5, are measured and used to provide information relating to the magnitudes of several parameters. These parameters, in a particularly preferred embodiment of the present invention, relate to the turbidity plateau value, the turbidity variability value, the conductivity plateau value, and the conductivity variability value. Each of these four magnitudes is measured during each of several preselected time periods. These preselected time periods typically coincide with rinse sequences of a washing cycle. The timing and methodology used to measure these parameters is described above.

Figure 6:
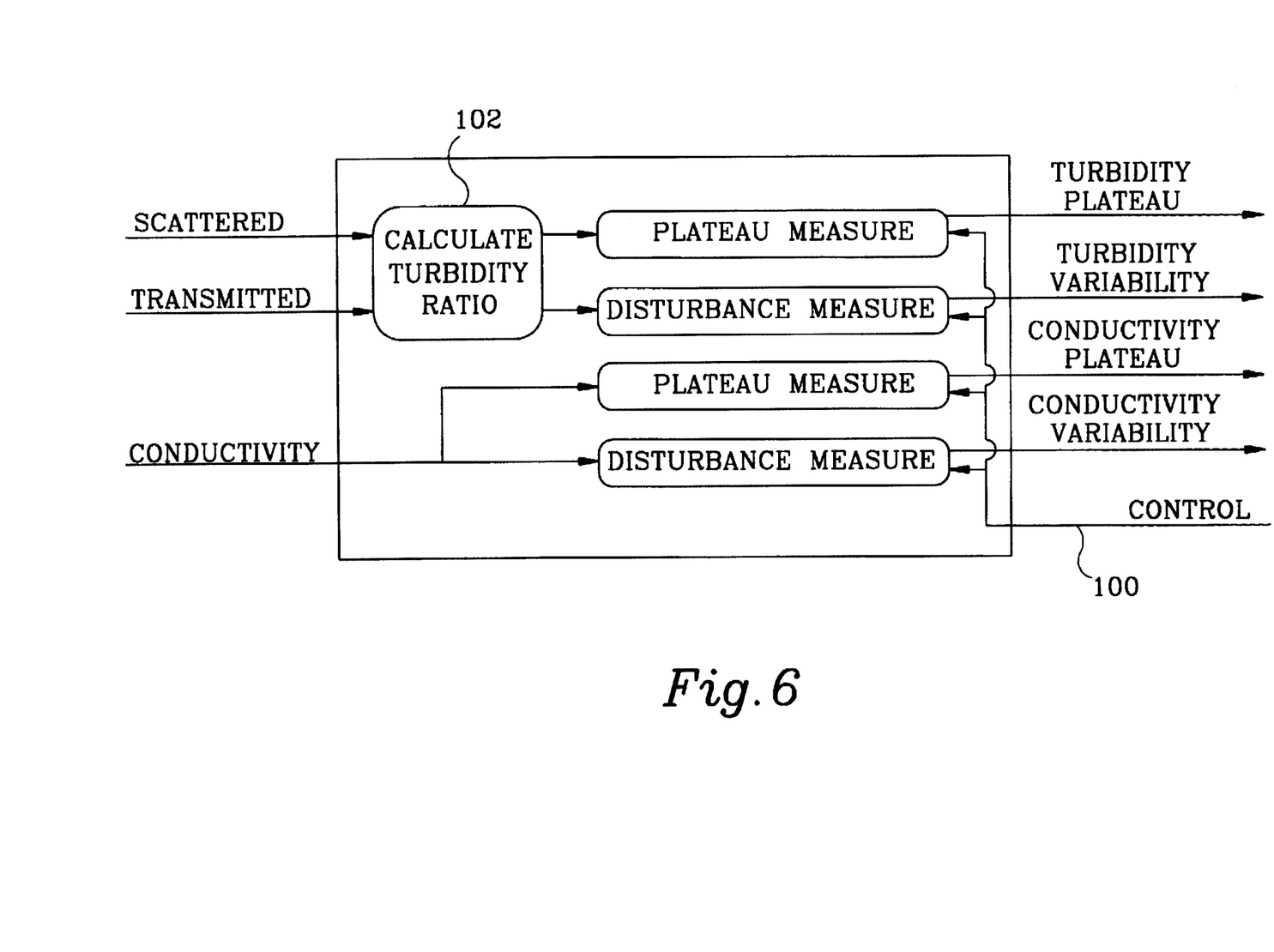
FIG. 6 represents the relationship between the input measurements and the output characterizations of the present invention.

FIG. 6 is a schematic representation of this procedure. All of the measurements are time based and are typically taken in response to a signal 100 from the appliance controller which indicates the time when the measurements should begin and when they should end. The time during which the measurement takes place is referred to as a measuring period. For example, the measuring period may start at the beginning of a rinse sequence and then stop at the end of the rinse sequence. This preselected period of time is determined by signals 100 received from the controller. The calculation of the turbidity ratio 102 in FIG. 6 is done by dividing the scattered turbidity signal by the transmitted turbidity signal. The turbidity ratio and the conductivity are both used to provide the plateau values and variability values described above. The plateau values are described above in conjunction with reference numerals 82 and 92 in FIGS. 4 and 5. The variability values are described above in conjunction with reference numerals 84 and 94 in FIGS. 4 and 5.

In a preferred embodiment of the present invention, fuzzy logic is used as a technique to translate the information relating to the plateau and variability values into information that relates to the characterization of the washing fluid. These characterizations are representative of the quantity of suspendeds, and solubles, and cycle state of the washing fluid. Naturally, it should be understood that techniques other than fuzzy logic can be employed for these purposes, but fuzzy logic is particularly applicable to this type of calculation procedure.

Figure 7:
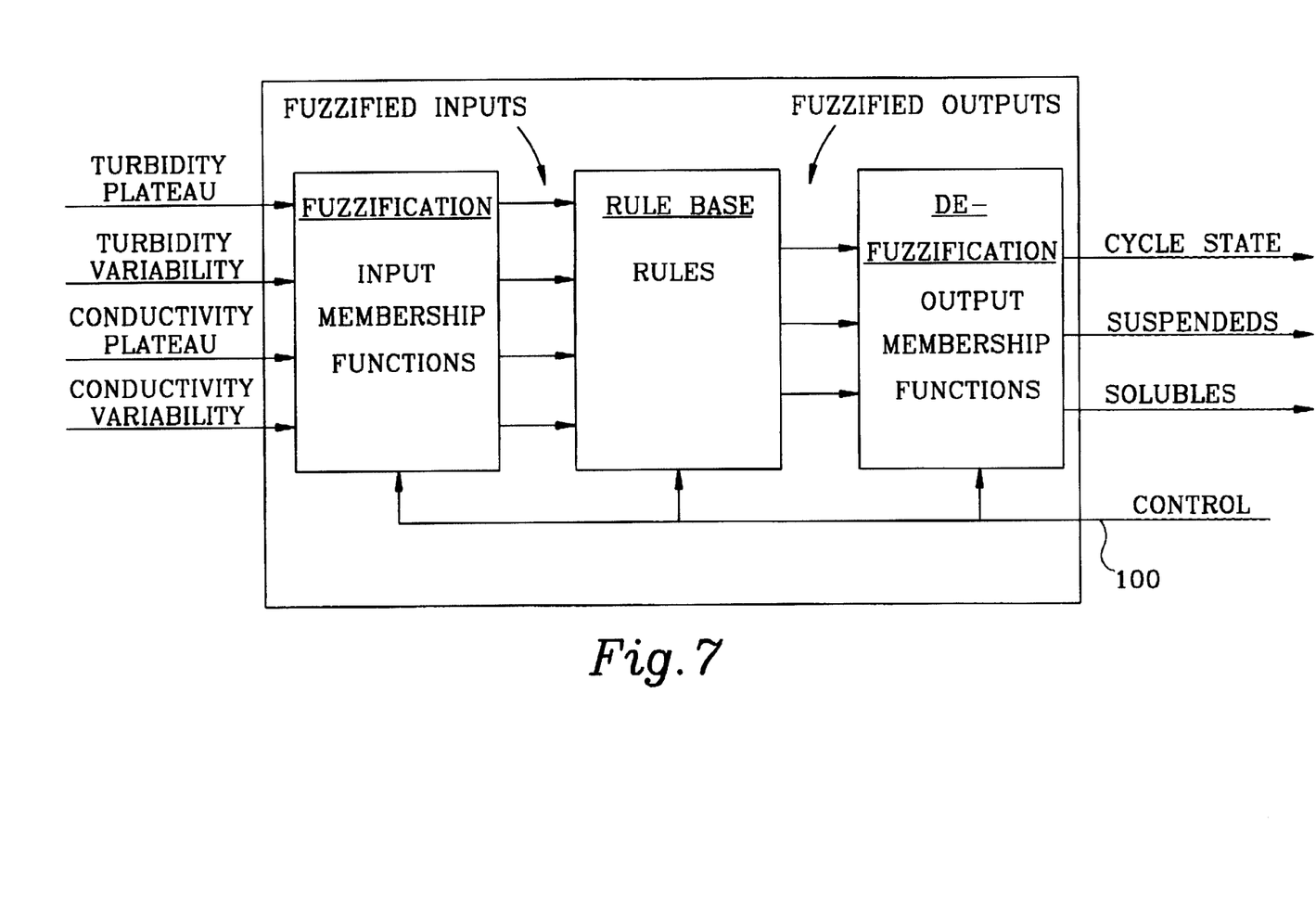
FIG. 7 is a schematic representation of the fuzzy logic engine.
Figure 8:
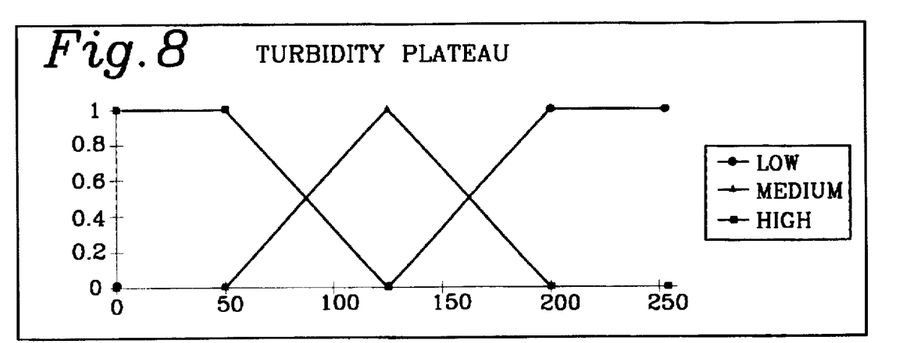
FIGS. 8–11 represent membership functions for the four measured input parameters to the fuzzy logic engine.
Figure 9:
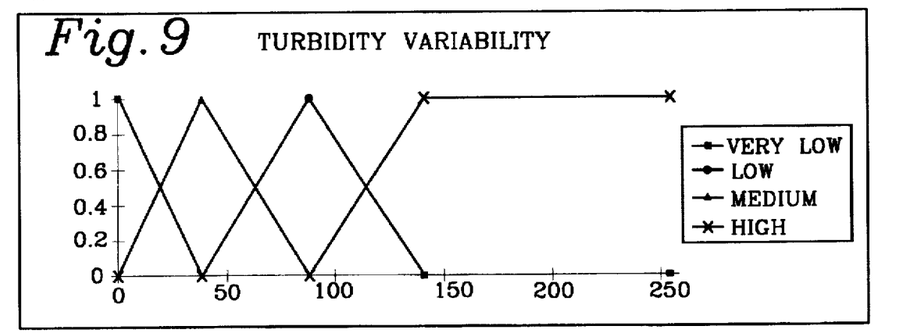
Figure 10:
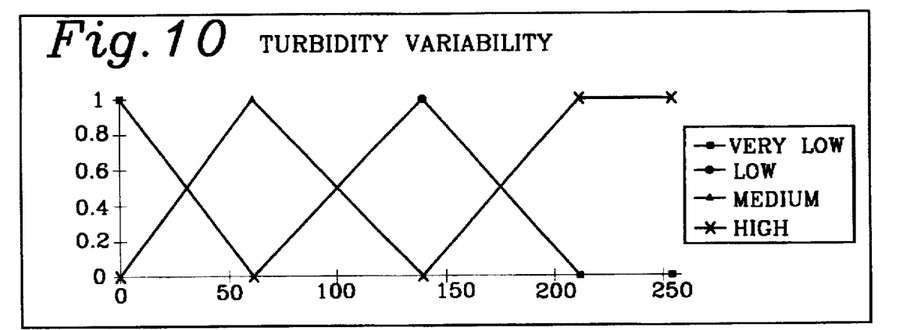
Figure 11:
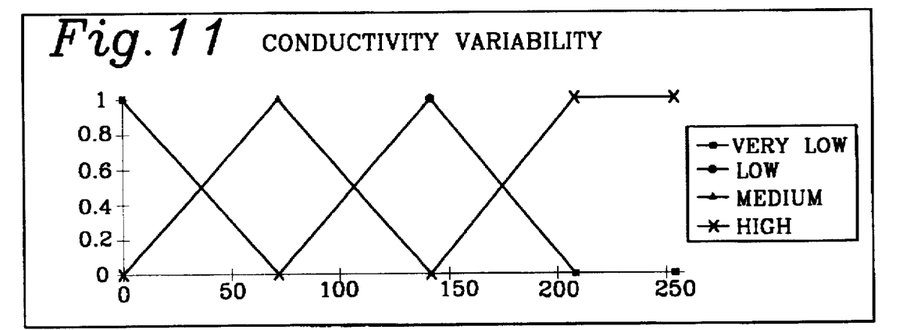

In FIG. 7, the use of fuzzy logic with respect to the input measurements and the output characterizations is illustrated schematically. As described above, the controller of the appliance provides a signal 100 which determines when the suspendeds, solubles and cycle state should be quantified. In other words, the controller of the washing machine determines when the fuzzy logic engine shown in FIG. 7 should be used. When the control signal 100 is received by the fuzzy logic engine, the parameter measurements are first fuzzified and provided as inputs to the rule base portion of the engine. Within the fuzzification block, each parameter measurement is provided with its own membership function that performs the fuzzification. The output from the rule base is provided, as three fuzzified characteristics, to a defuzzification section of the fuzzy logic engine. Within the defuzzification block, each characteristic is provided with its own membership function that performs the defuzzification. These membership functions are described below in greater detail.

FIGS. 8-14 show the various membership functions for turbidity plateau, turbidity variability, conductivity plateau, conductivity variability, solubles, suspendeds and cycle state. Using FIG. 9 as an example, the turbidity variability membership function has four terms, very low, low, medium and high. The "universe of discourse" or range for the turbidity variability is from zero to 255. The representations shown in FIGS. 8-14 are familiar to those skilled in the art of fuzzy logic and will not be described in greater detail herein.

The fuzzified inputs are provided into the rule base of the fuzzy logic engine. The rule base employs the traditional rule structure of premises and conclusions. However, the method of inference is unique to fuzzy logic and is explained further below. The rules shown immediately below represent some of the most dominate rules of the total rule set used in the rule base of the fuzzy logic engine used in a particularly preferred embodiment of the present invention.

IF (turbidity plateau is Low) AND (turbidity variability is Low) AND (conductivity plateau is High) AND (conductivity variability is Low) THEN (cycle state is Low) AND (suspendeds is Low) and (solubles is High)
IF (turbidity plateau is Low) AND (turbidity variability is Low) AND (conductivity plateau is Medium) AND (conductivity variability is Low) THEN (cycle state is Low) AND (suspendeds is Low) and (solubles is Medium)
IF (turbidity plateau is High) AND (turbidity variability is Low) AND -continued (conductivity plateau is Low) AND (conductivity variability is Low)THEN (cycle state is Medium) AND (suspendeds is Medium) and (solubles is Medium)
IF (turbidity plateau is Low) AND (turbidity variability is Medium) AND (conductivity plateau is Low) AND (conductivity variability is Medium)THEN (cycle state is Medium) AND (suspendeds is Medium) and (solubles is Medium)
IF (turbidity plateau is Low) AND (turbidity variability is Low) AND (conductivity plateau is Low) AND (conductivity variability is High) THEN (cycle state is Medium) AND (suspendeds is High) and (solubles is Low)
IF (turbidity plateau is High) AND (turbidity variability is Low) AND (conductivity plateau is High) AND (conductivity variability is Low) THEN (cycle state is High) AND (suspendeds is High) and (solubles is High)
IF (turbidity plateau is High) AND (turbidity variability is Low) AND (conductivity plateau is Low) AND (conductivity variability is Medium) THEN (cycle state is High) AND (suspendeds is High) and (solubles is Medium)
IF (turbidity plateau is Medium) AND (turbidity variability is Low) AND (conductivity plateau is Low) AND (conductivity variability is Low) THEN (cycle state is Low) AND (suspendeds is Medium) and (solubles is Low)
IF (turbidity plateau is Low) AND (turbidity variability is Medium) AND (conductivity plateau is Low) AND (conductivity variability is Medium) THEN (cycle state is Medium) AND (suspendeds is Medium) and (solubles is Medium)

Figure 12:
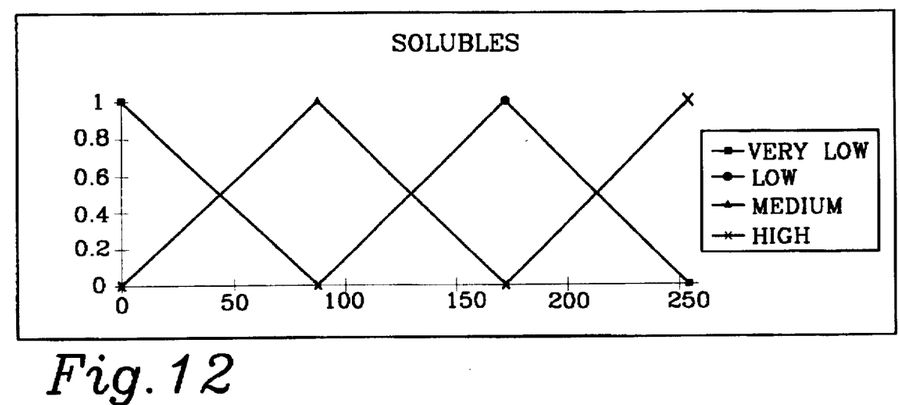
FIGS. 12, 13 and 14 illustrate the membership functions for the three output characterizations of the fuzzy logic engine.
Figure 13:
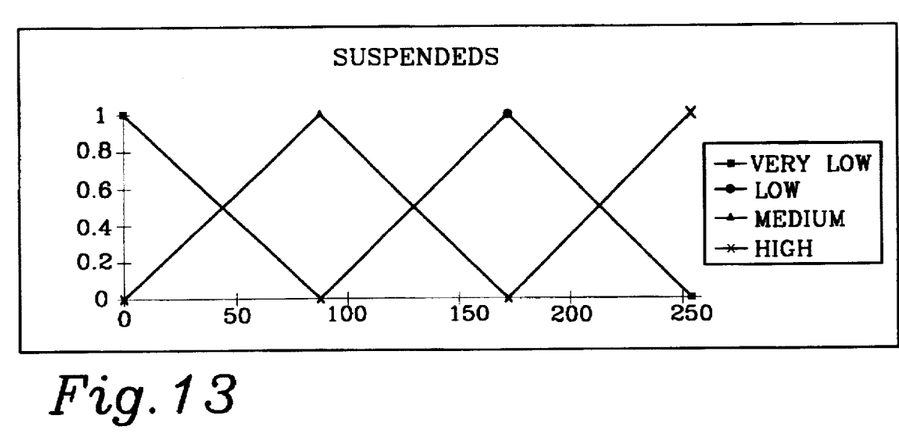
Figure 14:
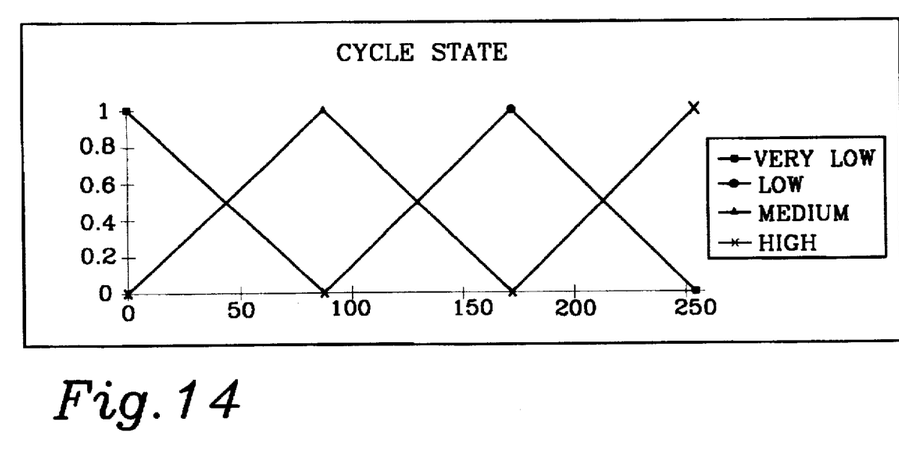

The technique for relating the premises of a rule to its conclusion is called inferencing. With fuzzy logic, there are several methods of inferencing which include: Min-Max, Max-Min and Max-Prod. A typical inference method is Max-Min. This method of inferencing is defined by first finding the minimum degree of membership of each of the premises of a rule. Then, that degree of membership is assigned to each of the conclusions of that rule. Once this is completed for all of the rules, the maximum degree of membership for each term of each conclusion is used for defuzzification. FIGS. 12, 13 and 14 are the membership functions used to defuzzify the outputs from the rule base which represent solubles, suspendeds and cycle state.

Figure 15:
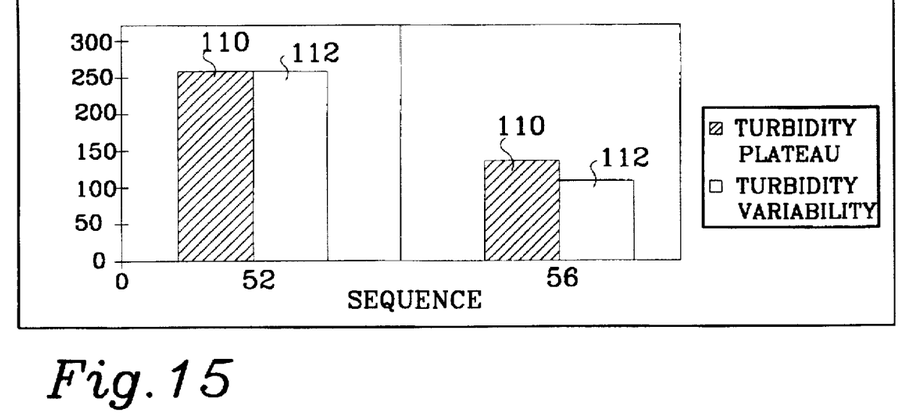
FIGS. 15 and 16 show the relative changes in the turbidity and conductivity measurements taken during the two rinse sequences of a hypothetical washing procedure.
Figure 16:
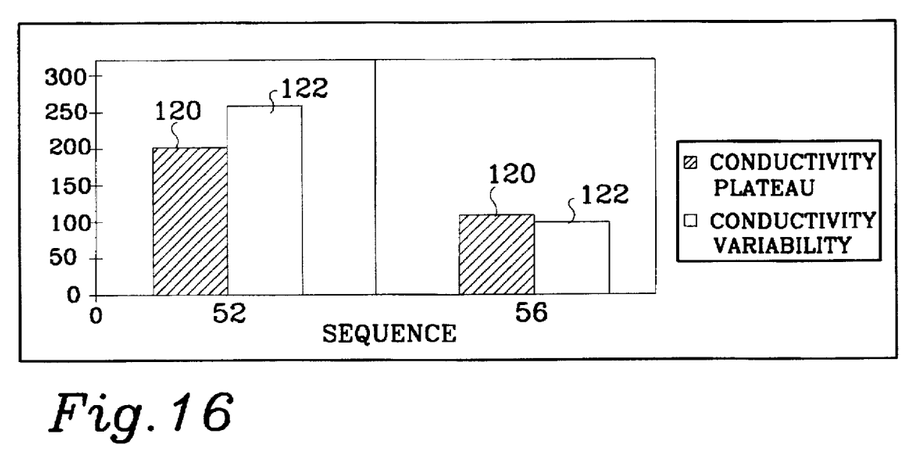
Figure 17:
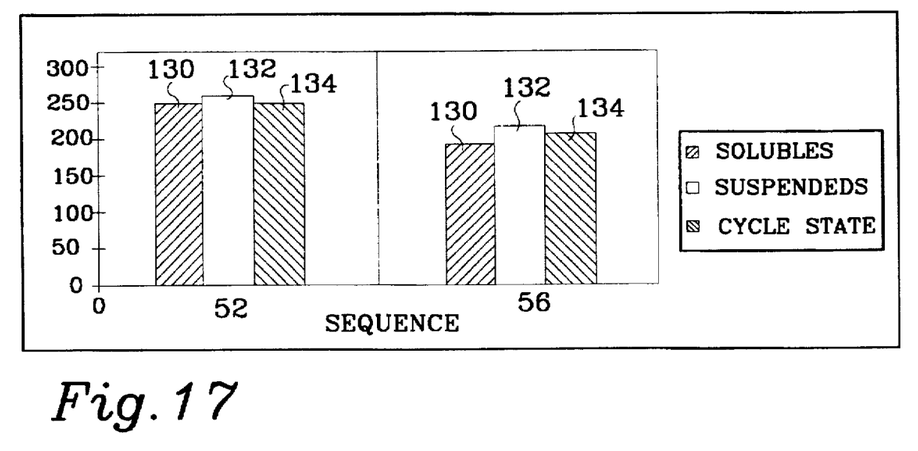
FIG. 17 shows the resulting characterizations in terms of solubles, suspendeds, and cycle state during the two rinse sequences of an exemplary washing procedure.

FIGS. 15, 16 and 17 are graphical representations of the changes of the turbidity parameters, the conductivity parameters and the resulting characterizations of the washing fluid, respectively. In FIG. 15, the bars 110 represent the turbidity plateau values measured during the two sequences, 52 and 56. The bars in FIG. 15 identified by reference numeral 112 represent the turbidity variability values measured during the two rinse sequences, 52 and 56.

With reference to FIG. 16, the bars identified by reference numerals 120 represent the conductivity plateau values measured during the two rinse sequences, 52 and 56, and reference numeral 122 represent the conductivity variability values measured during the two rinse sequences, 52 and 56. It should be understood that in FIGS. 15 and 16, the vertical axis represents a digitized value of the turbidity and conductivity parameters discussed above in conjunction with FIGS. 4 and 5.

FIG. 17 shows the results of the calculations of the present invention. The bars identified by reference numerals 130 show the calculated magnitudes of the solubles in the wash water during the two rinse sequences, 52 and 56. The bars identified by reference numerals 132 show the magnitudes of the suspendeds in the wash water during the two rinse sequences, 52 and 56. The bars identified by reference numerals 134 show the magnitudes of the cycle state in the wash water during the two rinse sequences, 52 and 56. The magnitudes shown in FIG. 17 are the end result of the process or method of the present invention. They represent the characterization of the washing fluid, in terms of solubles and suspendeds, and cycle state, that will allow a controller to make decisions that determine the number, order, and type of sequences in a cycle, the number, order, and type of actions in a sequence, and the number, order, and type of operations in an action. The measurements represented in FIGS. 15 and 16 are the digitized inputs to the fuzzy logic engine while the characterizations shown in FIG. 17 are the digitized outputs from the fuzzy logic engine during the two rinse sequences, 52 and 56.

Although the present invention has been described in terms of one particular embodiment, it should be understood that alternative embodiments can be achieved with minor modifications. The method of the present invention measures the plateau and variability for both turbidity and conductivity and uses these as the parameters that are measured. These parameters are used as a basis for calculating first, second and third characteristics of the fluid which, in a preferred embodiment, relate to the solubles and suspendeds in the wash water, and the cycle state of the wash water. However, it should be understood that other parameters, in place of the turbidity and conductivity, could be used as inputs that are measured and other characterizations, in place of the solubles, suspendeds and cycle state, could be calculated as outputs from the fuzzy logic engine.

The embodiments of the invention in which an exclusive property or right is claimed are defined as follows:

1. A method for characterizing the nature of a fluid, comprising:

measuring a first parameter relating to a turbidity of said fluid;

measuring a second parameter relating to a conductivity of said fluid;

calculating a first characteristic of said fluid as a function of said first and second parameters; and calculating a second characteristic of said fluid as a function of said first and second parameters.

2. The method of claim 1, further comprising:

calculating a third characteristic of said fluid as a function of said first and second parameters.

3. The method of claim 1, further comprising:

providing an output signal which is representative of said first and second characteristics.

4. The method of claim 2, further comprising:

providing an output signal which is representative of said first, second and third characteristics.

5. The method of claim 4, further comprising:

transmitting said output signal to a controller of a machine for washing articles.

6. The method of claim 1, wherein:

said first parameter comprises a first magnitude representative of a plateau value of turbidity during a first preselected time period and a second magnitude representative of a variability value of turbidity during a second preselected time period.

7. The method of claim 6, wherein:

said second parameter comprises a third magnitude representative of a plateau value of conductivity during a third preselected time period and a fourth magnitude representative of a variability value of conductivity during a fourth preselected time period.

8. The method of claim 1, wherein:

said first characteristic is representative of the magnitude of particulates suspended in said fluid.

9. The method of claim 1, wherein:

said second characteristic is representative of the magnitude of elements in solution within said fluid.

10. The method of claim 1, further comprising:

using a fuzzy logic technique to calculate said first and second characteristics.

11. The method of claim 2, further comprising:

using a fuzzy logic technique to calculate said first, second and third characteristics.

12. The method of claim 2, wherein:

said third characteristic is representative of a cycle state, said cycle state being representative of the overall magnitude of foreign matter within said fluid.

13. A method for characterizing the nature of a fluid, comprising:

measuring a first parameter relating to a turbidity of said fluid;

measuring a second parameter relating to a conductivity of said fluid;

calculating a first characteristic of said fluid as a function of said first and second parameters;

calculating a second characteristic of said fluid as a function of said first and second parameters; and calculating a third characteristic of said fluid as a function of said first and second parameters.

14. The method of claim 13, further comprising:

providing an output signal which is representative of said first, second and third characteristics; and transmitting said output signal to a controller of a machine for washing articles.

15. The method of claim 13, wherein:

said first parameter comprises a first magnitude representative of a plateau value of turbidity during a first preselected time period and a second magnitude representative of a variability value of turbidity during a second preselected time period and said second parameter comprises a third magnitude representative of a plateau value of conductivity during a third preselected time period and a fourth magnitude representative of a variability value of conductivity during a fourth preselected time period.

16. The method of claim 13, wherein:

said first characteristic is representative of the magnitude of particulates suspended in said fluid and said second characteristic is representative of the magnitude of elements in solution within said fluid.

17. The method of claim 13, further comprising:

using a fuzzy logic technique to calculate said first, second and third characteristics.

18. The method of claim 13, wherein:

said third characteristic is representative of a cycle state, said cycle state being representative of the overall magnitude of foreign matter within said fluid.

19. A method for characterizing the nature of a fluid, comprising:

measuring a first parameter relating to a turbidity of said fluid;

measuring a second parameter relating to a conductivity of said fluid;

calculating a first characteristic of said fluid as a function of said first and second parameters;

calculating a second characteristic of said fluid as a function of said first and second parameters;

calculating a third characteristic of said fluid as a function of said first and second parameters;

providing an output signal which is representative of said first, second and third characteristics; and transmitting said output signal to a controller of a machine for washing articles, said first parameter comprising a first magnitude representative of a plateau value of turbidity during a first preselected time period and a second magnitude representative of a variability value of turbidity during a second preselected time period and said second parameter comprises a third magnitude representative of a plateau value of conductivity during a third preselected time period and a fourth magnitude representative of a variability value of conductivity during a fourth preselected time period, said first characteristic being representative of the magnitude of particulates suspended in said fluid and said second characteristic is representative of the magnitude of elements in solution within said fluid, said third characteristic being representative of a cycle state, said cycle state being representative of the overall magnitude of foreign matter within said fluid.

20. The method of claim 19, further comprising:

using a fuzzy logic technique to calculate said first, second and third characteristics.

* * * * *